US012624009B2

(12) United States Patent
Wang et al.

(10) Patent No.: US 12,624,009 B2
(45) Date of Patent: May 12, 2026

(54) HYDRATE OF VEGFR INHIBITOR, CRYSTAL FORM THEREOF AND PREPARATION METHOD THEREFOR

(71) Applicant: CHENGDU EASTON BIOPHARMACEUTICALS CO., LTD, Chengdu (CN)

(72) Inventors: Leixin Wang, Chengdu (CN); Huike Gu, Chengdu (CN); Xiaochao Xian, Chengdu (CN); Hong Chen, Chengdu (CN); Ying Wang, Chengdu (CN)

(73) Assignee: CHENGDU EASTON BIOPHARMACEUTICALS CO., LTD, Chengdu (CN)

( * ) Notice: Subject to any disclaimer, the term of this patent is extended or adjusted under 35 U.S.C. 154(b) by 0 days.

(21) Appl. No.: 19/256,050

(22) Filed: Jun. 30, 2025

(65) Prior Publication Data

US 2025/0388552 A1 Dec. 25, 2025

Related U.S. Application Data

(63) Continuation of application No. PCT/CN2024/096724, filed on May 31, 2024.

(30) Foreign Application Priority Data

Jun. 2, 2023 (CN) ......................... 202310647472.5
Nov. 20, 2023 (CN) ......................... 202311552719.1
Jan. 26, 2024 (CN) ......................... 202410117086.X

(51) Int. Cl.
*C07D 239/88* (2006.01)
*B01D 9/00* (2006.01)

(52) U.S. Cl.
CPC ......... *C07D 239/88* (2013.01); *B01D 9/0036* (2013.01); *B01D 9/0081* (2013.01); *B01D 2009/0086* (2013.01)

(58) Field of Classification Search
CPC .. C07D 239/88; B01D 9/0036; B01D 9/0081; B01D 2009/0086
See application file for complete search history.

(56) References Cited

U.S. PATENT DOCUMENTS

2021/0155613 A1* 5/2021 Sheng ................ A61K 31/4709

FOREIGN PATENT DOCUMENTS

| | | | |
|---|---|---|---|
| CN | 105777722 | A | 7/2016 |
| CN | 106604919 | A | 4/2017 |
| CN | 109641056 | A | 4/2019 |
| CN | 106604919 | * | 11/2019 |
| CN | 106604919 | B | 11/2019 |
| CN | 116987069 | A | 11/2023 |

OTHER PUBLICATIONS

Zhang, Ying et al., "Fruquintinib: a novel antivascular endothelial growth factor receptor tyrosine kinase inhibitor for the treatment of metastatic colorectal cancer", Cancer Management and Research, Aug. 16, 2019, vol. 2019, No. 11, pp. 7787-7803.

* cited by examiner

*Primary Examiner* — D Margaret M Seaman
(74) *Attorney, Agent, or Firm* — NKL Law; Allen Xue

(57) ABSTRACT

A hydrate of a VEGFR inhibitor, a crystal form thereof and a preparation method therefor are provided. The VEGFR inhibitor is 6-(6,7-dimethoxyquinazolin-4-yl-oxy)-N,2-dimethylbenzofuran-3-carboxamide, and the hydrate and the crystal form thereof have good physicochemical properties, and have good flowability, solubility, stability and bioavailability, and alleviated hygroscopicity. In addition, the preparation method is simple, has good repeatability, achieves high yield, and is easy to perform and environment-friendly, and the method requires only a small amount of solvents and facilitates recycling use, thus effectively reducing the cost on reagents, and enabling easy implementation of large-scale mass production.

20 Claims, 10 Drawing Sheets

HYDRATE OF VEGFR INHIBITOR, CRYSTAL FORM THEREOF AND PREPARATION METHOD THEREFOR

CROSS-REFERENCE TO RELATED APPLICATIONS

The present application is a continuation of PCT International Application No. PCT/CN2024/096724, filed on May 31, 2024, which claims the priority to the prior application with the patent application No. 202310647472.5 filed with China National Intellectual Property Administration on Jun. 2, 2023, the prior application with the patent application No. 202311552719.1 filed with China National Intellectual Property Administration on Nov. 20, 2023, and the prior application with the patent application No. 202410117086.X filed with China National Intellectual Property Administration on Jan. 26, 2024, the content of each is incorporated herein by reference in its entirety.

TECHNICAL FIELD

The present application relates to the field of pharmaceutical crystal forms, in particular to a hydrate of a VEGFR inhibitor, a crystal form thereof, and a preparation method therefor.

BACKGROUND

Fruquintinib (trade name: Elunate) is a VEGFR inhibitor developed by Hutchison Whampoa Limited for the treatment of metastatic colorectal cancer, and its original formulation Elunate was approved for marketing in China on Sep. 4, 2018. Fruquintinib has a structure represented by formula (I) below:

formula (I)

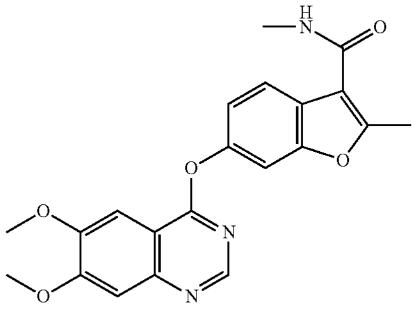

In the prior art, CN106604919B discloses six crystal forms of fruquintinib, i.e., crystal form I, crystal form II, crystal form III, crystal form VII, crystal form IV, and crystal form VIII. The crystal forms are all anhydrates or organic solvates. No fruquintinib hydrates and crystal forms thereof with good druggability have been developed in the prior art. Therefore, there is a need to further develop a hydrate form of fruquintinib and a crystal form thereof.

SUMMARY

In view of the problems described above in the prior art, the present application provides a hydrate of a VEGFR inhibitor, a crystal form thereof, and a preparation method therefor. The VEGFR inhibitor is fruquintinib, with the chemical name of 6-(6,7-dimethoxyquinazolin-4-yl-oxy)-N,2-dimethylbenzofuran-3-carboxamide.

In a first aspect of the present application, provided is a fruquintinib hydrate.

The hydrate has a structural formula shown in formula (II) below:

II

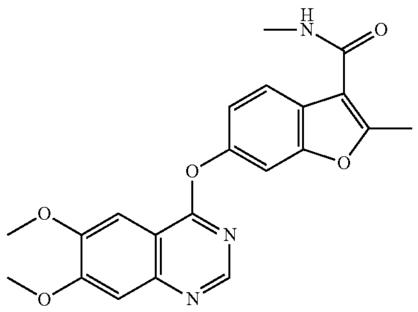

$\cdot nH_2O$, wherein n is 0.5-3.

In some embodiments of the present application, n is 0.5, 1, 2, or 3.

In some embodiments of the present application, the hydrate is a fruquintinib trihydrate.

In some embodiments of the present application, provided is a crystal form of the fruquintinib hydrate, and an X-ray powder diffraction pattern of the crystal form has characteristic peaks at 2θ angles of 7.2±0.2°, 8.6±0.2°, 14.4±0.2°, 15.2±0.2°, 20.4±0.2°, 22.3±0.2°, 24.0±0.2°, 26.1±0.2°, 26.4±0.2°, and 29.1±0.2°.

In some embodiments of the present application, the X-ray powder diffraction pattern of the hydrate crystal form has characteristic peaks at 2θ angles of 7.212±0.2°, 8.643±0.2°, 14.445±0.2°, 15.182±0.2°, 20.423±0.2°, 22.348±0.2°, 23.960±0.2°, 26.100±0.2°, 26.446±0.2°, and 29.119±0.2°.

In some embodiments of the present application, the X-ray powder diffraction pattern of the hydrate crystal form has characteristic peaks at 2θ angles of 4.9±0.2°, 7.2±0.2°, 8.6±0.2°, 12.0±0.2°, 14.4±0.2°, 15.2±0.2°, 16.2±0.2°, 20.4±0.2°, 22.3±0.2°, 24.0±0.2°, 25.4±0.2°, 26.1±0.2°, 26.4±0.2°, 28.3±0.2°, and 29.1±0.2°.

In some embodiments of the present application, the X-ray powder diffraction pattern of the hydrate crystal form has characteristic peaks at 2θ angles of 4.861±0.2°, 7.212±0.2°, 8.643±0.2°, 12.018±0.2°, 14.445±0.2°, 15.182±0.2°, 16.171±0.2°, 20.423±0.2°, 22.348±0.2°, 23.960±0.2°, 25.370±0.2°, 26.100±0.2°, 26.446±0.2°, 28.326±0.2°, and 29.119±0.2°.

In some embodiments of the present application, the X-ray powder diffraction pattern of the hydrate crystal form has characteristic peaks at 2θ angles of 4.9±0.2°, 7.2±0.2°, 8.6±0.2°, 12.0±0.2°, 14.4±0.2°, 15.2±0.2°, 16.2±0.2°, 17.3±0.2°, 20.4±0.2°, 22.3±0.2°, 24.0±0.2°, 24.4±0.2°, 25.4±0.2°, 26.1±0.2°, 26.4±0.2°, 28.3±0.2°, 28.6±0.2°, 29.1±0.2°, 29.6±0.2°, and 32.7±0.2°.

In some embodiments of the present application, the X-ray powder diffraction pattern of the hydrate crystal form has characteristic peaks at 2θ angles of 4.861±0.2°, 7.212±0.2°, 8.643=0.2°, 12.018±0.2°, 14.445±0.2°, 15.182±0.2°, 16.171±0.2°, 17.316±0.2°, 20.423±0.2°, 22.348±0.2°, 23.960±0.2°, 24.428±0.2°, 25.370±0.2°, 26.100±0.2°, 26.446±0.2°, 28.326±0.2°, 28.610±0.2°, 29.119±0.2°, 29.598±0.2°, and 32.656±0.2°.

In some embodiments of the present application, the X-ray powder diffraction pattern of the hydrate crystal form has characteristic peaks at 2θ angles of 4.9±0.2°, 7.2±0.2°, 8.6±0.2°, 9.7±0.2°, 12.0±0.2°, 14.4±0.2°, 15.2±0.2°, 16.2±0.2°, 17.3±0.2°, 20.4±0.2°, 22.3±0.2°, 24.0±0.2°, 24.4±0.2°, 25.4±0.2°, 26.1±0.2°, 26.4±0.2°, 28.3±0.2°, 28.6±0.2°, 29.1±0.2°, 29.6±0.2°, and 32.7±0.2°.

In some embodiments of the present application, the X-ray powder diffraction pattern of the hydrate crystal form has characteristic peaks at 2θ angles of 4.861±0.2°, 7.212±0.2°, 8.643±0.2°, 9.7064±0.2°, 12.018±0.2°, 14.445±0.2°, 15.182±0.2°, 16.171±0.2°, 17.316±0.2°, 20.423±0.2°, 22.348±0.2°, 23.960±0.2°, 24.428±0.2°, 25.370±0.2°, 26.100±0.2°, 26.446±0.2°, 28.326±0.2°, 28.610±0.2°, 29.119±0.2°, 29.598±0.2°, and 32.656±0.2°.

In some specific embodiments of the present application, the X-ray powder diffraction pattern of the hydrate crystal form is substantially as shown in FIG. 1A.

In some embodiments of the present application, the X-ray powder diffraction pattern of the hydrate crystal form has characteristic peaks at 2θ angles of 4.8±0.2°, 7.2±0.2°, 8.6=0.2°, 9.7±0.2°, 12.0±0.2°, 14.4±0.2°, 15.2±0.2°, 16.2±0.2°, 17.3±0.2°, 19.9±0.2°, 20.4±0.2°, 21.8±0.2°, 22.3±0.2°, 24.0±0.2°, 24.3±0.2°, 25.4±0.2°, 26.0±0.2°, 26.4±0.2°, 28.2±0.2°, 28.6±0.2°, 29.1±0.2°, 29.6±0.2°, and 32.7±0.2°.

In some specific embodiments of the present application, the X-ray powder diffraction pattern of the hydrate crystal form is shown in FIG. 1B.

In some specific embodiments of the present application, the X-ray powder diffraction pattern of the hydrate crystal form is shown in FIG. 1C.

In some embodiments of the present application, a DSC profile of the hydrate crystal form has endothermic peaks at 95.23±5° C. and 245.71±5° C.

In some specific embodiments of the present application, the DSC profile of the hydrate crystal form is substantially as shown in FIG. 2A.

In some specific embodiments of the present application, a TGA profile of the hydrate crystal form is substantially as shown in FIG. 3.

In some specific embodiments of the present application, the hydrate crystal form has a water content of 11.00±2.0%. For example, the hydrate crystal form has a water content of 11.50%, 11.60%, 11.70%, 11.80%, 11.90%, 12.00%, 12.05%, 12.07%, 12.10%, 12.20%, 12.30%, 12.40%, or 12.50%.

In some specific embodiments of the present application, the hydrate crystal form has a water content of 11.90±0.20%.

In some specific embodiments of the present application, the hydrate crystal form has a water content of 11.90%.

In some specific embodiments of the present application, the hydrate crystal form is a triclinic crystal system, with a space group of P-1 (No. 2); a molecular weight of 447.44 $g \cdot mol^{-1}$; Z' of 1; the following unit cell parameters: α=4.880 (5) Å, b=11.98 (2) Å, c=17.916 (17) Å, α=89.10 (6)°, β=94.56 (10)°, and γ=97.09 (18)°; and a unit cell volume of V=1036 (2) Å3.

In a second aspect of the present application, provided is a crystal form α of fruquintinib, and an X-ray powder diffraction pattern of the crystal form has characteristic peaks at 2θ angles of 7.2±0.2°, 8.6±0.2°, 14.4±0.2°, 15.2±0.2°, 20.4±0.2°, 22.3±0.2°, 24.0±0.2°, 26.1±0.2°, 26.4±0.2°, and 29.1±0.2°.

In some embodiments of the present application, the X-ray powder diffraction pattern of the crystal form α has characteristic peaks at 2θ angles of 7.212±0.2°, 8.643±0.2°, 14.445±0.2°, 15.182±0.2°, 20.423±0.2°, 22.348±0.2°, 23.960±0.2°, 26.100±0.2°, 26.446±0.2°, and 29.119±0.2°.

In some embodiments of the present application, the X-ray powder diffraction pattern of the crystal form α has characteristic peaks at 2θ angles of 4.9±0.2°, 7.2±0.2°, 8.6±0.2°, 12.0±0.2°, 14.4=0.2°, 15.2±0.2°, 16.2±0.2°, 20.4±0.2°, 22.3±0.2°, 24.0±0.2°, 25.4±0.2°, 26.1±0.2°, 26.4±0.2°, 28.3±0.2°, and 29.1±0.2°.

In some embodiments of the present application, the X-ray powder diffraction pattern of the crystal form α has characteristic peaks at 2θ angles of 4.861±0.2°, 7.212±0.2°, 8.643±0.2°, 12.018±0.2°, 14.445±0.2°, 15.182±0.2°, 16.171±0.2°, 20.423±0.2°, 22.348±0.2°, 23.960±0.2°, 25.370±0.2°, 26.100±0.2°, 26.446±0.2°, 28.326±0.2°, and 29.119±0.2°.

In some embodiments of the present application, the X-ray powder diffraction pattern of the crystal form α has characteristic peaks at 2θ angles of 4.9±0.2°, 7.2±0.2°, 8.6±0.2°, 12.0±0.2°, 14.4±0.2°, 15.2±0.2°, 16.2±0.2°, 17.3±0.2°, 20.4±0.2°, 22.3±0.2°, 24.0±0.2°, 24.4±0.2°, 25.4±0.2°, 26.1±0.2°, 26.4±0.2°, 28.3±0.2°, 28.6±0.2°, 29.1±0.2°, 29.6±0.2°, and 32.7±0.2°.

In some embodiments of the present application, the X-ray powder diffraction pattern of the crystal form α has characteristic peaks at 2θ angles of 4.861±0.2°, 7.212±0.2°, 8.643±0.2°, 12.018=0.2°, 14.445±0.2°, 15.182±0.2°, 16.171±0.2°, 17.316±0.2°, 20.423±0.2°, 22.348±0.2°, 23.960±0.2°, 24.428±0.2°, 25.370±0.2°, 26.100±0.2°, 26.446±0.2°, 28.326±0.2°, 28.610±0.2°, 29.119±0.2°, 29.598±0.2°, and 32.656±0.2°.

In some embodiments of the present application, the X-ray powder diffraction pattern of the crystal form α has characteristic peaks at 2θ angles of 4.9±0.2°, 7.2±0.2°, 8.6±0.2°, 9.7±0.2°, 12.0±0.2°, 14.4±0.2°, 15.2±0.2°, 16.2±0.2°, 17.3±0.2°, 20.4±0.2°, 22.3±0.2°, 24.0±0.2°, 24.4±0.2°, 25.4±0.2°, 26.1±0.2°, 26.4±0.2°, 28.3±0.2°, 28.6±0.2°, 29.1±0.2°, 29.6±0.2°, and 32.7±0.2°.

In some embodiments of the present application, the X-ray powder diffraction pattern of the crystal form α has characteristic peaks at 2θ angles of 4.861±0.2°, 7.212±0.2°, 8.643±0.2°, 9.7064=0.2°, 12.018±0.2°, 14.445±0.2°, 15.182±0.2°, 16.171±0.2°, 17.316±0.2°, 20.423±0.2°, 22.348±0.2°, 23.960±0.2°, 24.428±0.2°, 25.370±0.2°, 26.100±0.2°, 26.446±0.2°, 28.326±0.2°, 28.610±0.2°, 29.119±0.2°, 29.598±0.2°, and 32.656±0.2°.

In some specific embodiments of the present application, the X-ray powder diffraction pattern of the crystal form α is substantially as shown in FIG. 1A.

In some embodiments of the present application, a DSC profile of the crystal form α has endothermic peaks at 95.23±5° C. and 245.71±5° C.

In some specific embodiments of the present application, the DSC profile of the crystal form α is substantially as shown in FIG. 2A.

In some specific embodiments of the present application, a TGA profile of the crystal form α is substantially as shown in FIG. 3.

In some specific embodiments of the present application, the crystal form α has a water content of 11.00±2.0%. For example, the crystal form α has a water content of 11.50%, 11.60%, 11.70%, 11.80%, 11.90%, 12.00%, 12.10%, 12.20%, 12.30%, 12.40%, or 12.50%.

In some specific embodiments of the present application, the crystal form α has a water content of 11.90±0.20%.

In some specific embodiments of the present application, the crystal form α has a water content of 11.90%.

In some specific embodiments of the present application, the crystal form α is a triclinic crystal system, with a space group of P-1 (No. 2); a molecular weight of 447.44 g·mol$^{-1}$; Z' of 1; the following unit cell parameters: α=4.880 (5) Å, b=11.98 (2) Å, c=17.916 (17) Å, α=89.10 (6)°, β94.56(10)°, and γ=97.09 (18)°; and a unit cell volume of V=1036 (2) Å3.

In some specific embodiments of the present application, the crystal form α is a hydrate having a structural formula shown in formula (II) below:

II

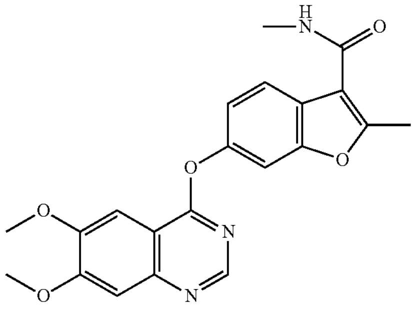

$\cdot n H_2O$, wherein n is 0.5-3.

In some embodiments of the present application, n is 0.5, 1, 2, or 3.

In some embodiments of the present application, the hydrate crystal form is a fruquintinib trihydrate.

In a third aspect of the present application, provided is a preparation method for the hydrate and the crystal form thereof according to the first aspect, and the crystal form α of fruquintinib according to the second aspect, the method comprising: mixing fruquintinib and an additive in a solvent A and crystallizing.

In some embodiments of the present application, the preparation method specifically comprises: mixing fruquintinib and an additive in a solvent A, ultrasonically dissolving the mixture, and allowing to stand for crystallization.

In some embodiments of the present application, the ultrasonic dissolution is performed at a temperature of 10-25° C.

In some embodiments of the present application, the ultrasonic dissolution is performed for an ultrasonic treatment period of 5-24 h, preferably 12 h.

In some embodiments of the present application, the standing for crystallization is performed at a crystallization temperature of 0-10° C., preferably 5° C.

In some embodiments of the present application, the standing for crystallization is performed for a standing period of 1-10 days, preferably 5 days.

In some embodiments of the present application, the additive is a polyol;

preferably, the polyol is a sugar alcohol;

more preferably, the polyol is selected from one or more of xylitol, mannitol, sorbitol, isomaltitol, and maltitol;

most preferably, the polyol is xylitol.

In some embodiments of the present application, the solvent A is an ether solvent;

preferably, the ether solvent is selected from one or more of tetrahydrofuran, diethyl ether, propylene glycol methyl ether, methyl tert-butyl ether, isopropyl ether, and 1,4-dioxane;

more preferably, the ether solvent is tetrahydrofuran.

In some embodiments of the present application, fruquintinib and the additive are in a mass ratio of (5-20):1, preferably 10:1.

In some embodiments of the present application, fruquintinib and the solvent A are in a mass-to-volume ratio of 1:(50-100), preferably 1:62.

In some specific embodiments of the present application, after the standing for crystallization, the resulting solid is collected and stored under an inert gas atmosphere.

In some specific embodiments of the present application, the storage is performed at a temperature of 5-10° C.

In some specific embodiments of the present application, the inert gas is nitrogen, argon, or helium, preferably nitrogen.

In a fourth aspect of the present application, provided is a preparation method for the hydrate and the crystal form thereof according to the first aspect, and the crystal form α of fruquintinib according to the second aspect, the method comprising:

(1) mixing fruquintinib in a solvent B, and heating for dissolution; and (2) adding a crystal seed of the hydrate or the crystal form thereof or the crystal form α and crystallizing.

In some embodiments of the present application, the heating for dissolution is heating to a reflux temperature for dissolution.

In some embodiments of the present application, in step (1), fruquintinib and the solvent B are in a mass ratio of 1:(3-40), e.g., 1:40, 1:36.7, 1:27.36, 1:10, 1:4.1, or 1:3.

In some embodiments of the present application, in step (1), fruquintinib and the solvent B are in a mass ratio of 1:(3-10), preferably 1:4.1.

In some embodiments of the present application, the solvent B is a mixed solvent of water and an ether solvent; water and the ether solvent are preferably in a mass ratio of 1:(1-9), more preferably 1:3.1;

preferably, the ether solvent in the solvent B is selected from one or more of tetrahydrofuran, diethyl ether, propylene glycol methyl ether, methyl tert-butyl ether, isopropyl ether, and 1,4-dioxane;

more preferably, the ether solvent in the solvent B is tetrahydrofuran.

In some embodiments of the present application, the crystal seed is used in an amount that is 1-20%, preferably 5%, of a feeding amount of fruquintinib in step (1) by mass fraction.

In some embodiments of the present application, step (2) specifically comprises: adding the crystal seed, cooling, and stirring for suspension crystallization;

preferably, step (2) specifically comprises: adding the crystal seed, cooling to 0-10° C., and stirring for suspension crystallization for 12-48 h;

more preferably, step (2) specifically comprises: adding the crystal seed, cooling to 5° C., and stirring for suspension crystallization for 24 h.

In some embodiments of the present application, the preparation method further comprises a step of preparing the crystal seed, which comprises: mixing fruquintinib and an additive in a solvent B and crystallizing.

In some embodiments of the present application, the preparation method for the hydrate or the crystal form thereof, or the crystal form α comprises:

(a) preparing a crystal seed of the crystal form α: mixing fruquintinib and an additive in a solvent A and crystallizing;

(b) mixing fruquintinib in a solvent B, and heating the mixture to reflux to give a solution; and (c) adding the crystal seed of the crystal form α and crystallizing.

The additive, the solvent A, and the solvent B are as defined above.

The hydrate or the crystal form thereof or the crystal form α prepared by the preparation method according to the third aspect of the present application can be used as a crystal seed in step (2) of the preparation method according to the fourth aspect.

The hydrate or the crystal form thereof or the crystal form α prepared according to the fourth aspect of the present application can also be used as a crystal seed in step (2) according to the fourth aspect.

The crystal form α of fruquintinib according to the second aspect of the present application is prepared by the preparation method according to the third or fourth aspect.

The fruquintinib hydrate and the crystal form thereof according to the first aspect of the present application are prepared by the preparation method according to the third or fourth aspect.

Compared with the prior art, the present application has the following beneficial effects:

(1) The inventors have found that in the prior art, CN106604919B has disclosed that the crystal form II is a hemiethanol solvate, the crystal form IV is a monoacetic acid solvate, the crystal form VIII is a monodioxane solvate, and the crystal form I, crystal form III, and crystal form VII are all anhydrous crystal forms, wherein the crystal forms used as solvates all contain organic solvents and are not suitable for drug development, and the anhydrous crystal forms are unstable, for example, the anhydrous crystal forms are at risk of being converted into hydrates when exposed to moisture, or are easily converted into the corresponding hydrates during processing and storage. Meanwhile, the inventors found that the crystal form C disclosed in CN105777722 A is also an anhydrate.

(2) In the present disclosure, a fruquintinib hydrate and a hydrate crystal form α are obtained for the first time, which have relatively good physicochemical properties, also exhibit relatively good flowability, solubility, stability, and bioavailability, and improved hygroscopicity, especially have good stability in water, and can be used for a wider medicament preparation process, such as wet granulation, thereby facilitating the improvement of the controllability and safety of drug quality.

(3) The preparation process of the fruquintinib hydrate and the hydrate crystal form α involved in the present disclosure is simple, exhibits good repeatability and high yield, and is easy to operate and green and environmentally friendly, and the preparation process requires a small amount of solvents and facilitates the recycling, thereby effectively reducing reagent costs, and enabling easy implementation of large-scale mass production.

DETAILED DESCRIPTION

In order to make the present application more comprehensible, the present application will be described in detail below with reference to the examples. However, these examples are only illustrative and are not limited to the application scope of the present application.

Terms used in the present application are explained as follows:

XRD: X-Ray Powder Diffraction

The X-ray powder diffraction (XRD) described in the present application was determined and collected using a Malvern-Panalytical Empyrean X-ray powder diffractometer. The specific parameters are shown in the table below:

TABLE 1

| | | | |
|---|---|---|---|
| Model of instrument | Empyrean | | |
| Manufacturer of instrument | Malvern-Panalytical | | |
| Target | Cu target (Cu-Kα radiation) | Wavelength | 1.5406 Å |
| Light tube voltage | 45 kV | Light tube current | 40 mA |
| Scanning range | 3-40° (2θ) | Step size | 0.013° |

Figure 1A:
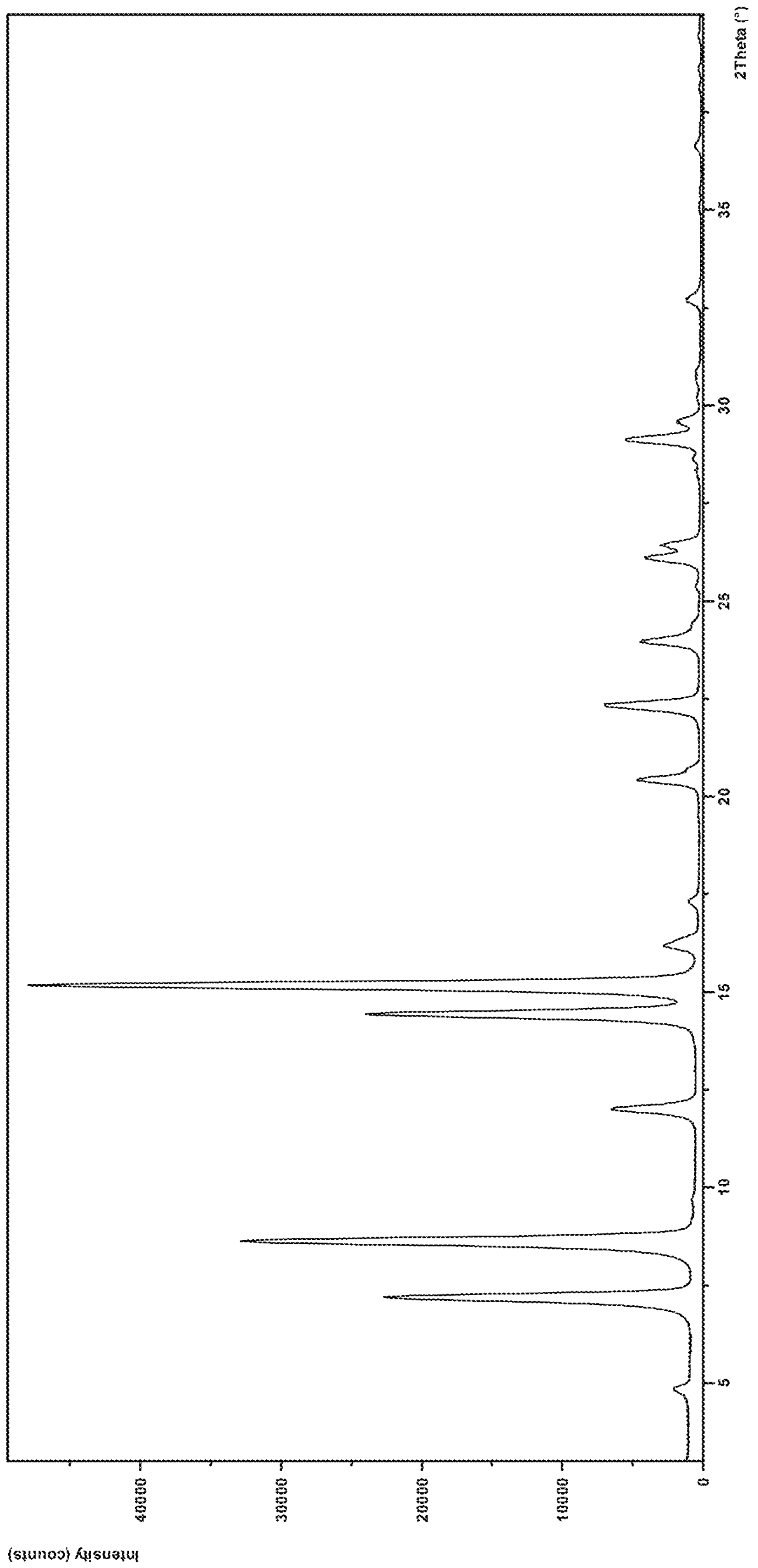
FIG. 1A shows an XRD pattern of a crystal form α of fruquintinib.

Herein, "the X-ray powder diffraction pattern is substantially as shown in FIG. 1A" means that the X-ray powder diffraction pattern is substantially the same as in FIG. 1A, and the term "substantially the same" in the X-ray powder diffraction pattern means that representative peak positions and intensity changes are taken into account.

DSC: Differential Scanning Calorimetry Analysis

The differential scanning calorimetry (DSC) described in the present application was determined and collected using METTLER TOLEDO model DSC-1, with a temperature ramp rate of 10° C./min, a temperature range of 25-250° C., and a nitrogen purge rate of 60 mL/min during the determination.

Figure 2A:
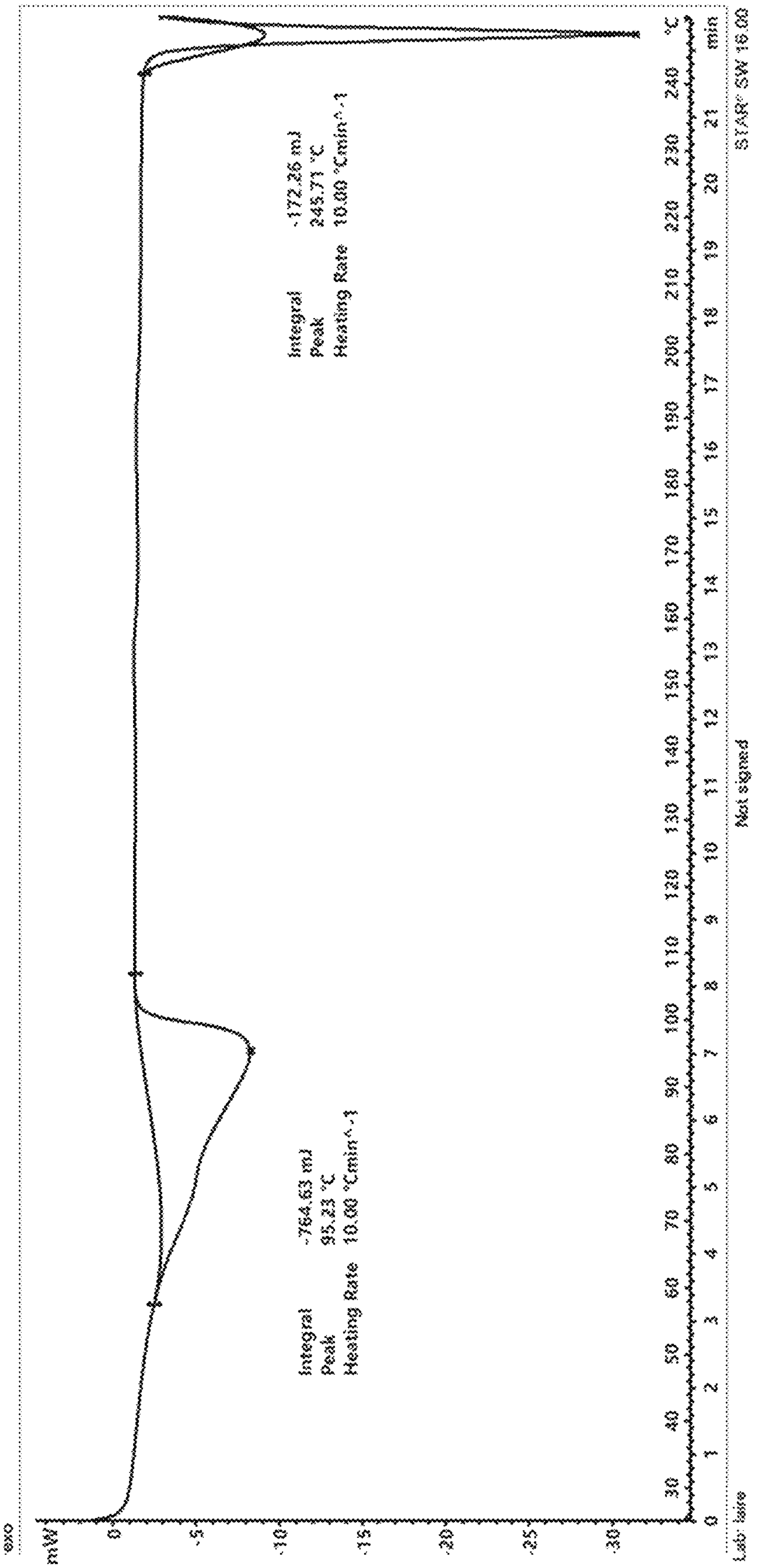
FIG. 2A shows a DSC profile of the crystal form α of fruquintinib.

Herein, "the DSC profile is substantially as shown in FIG. 2A" means that the DSC profile is substantially the same as in FIG. 2A, and the term "substantially the same" in the DSC profile means that representative characteristic peak positions are taken into account.

TGA: Thermogravimetric Analysis

The thermogravimetric analysis (TGA) described in the present application was determined and collected using METTLER TOLEDO model TGA-2, with a temperature ramp rate of 10° C./min, a temperature range of 30-300° C., and a nitrogen purge rate of 20 mL/min during the determination.

Figure 3:
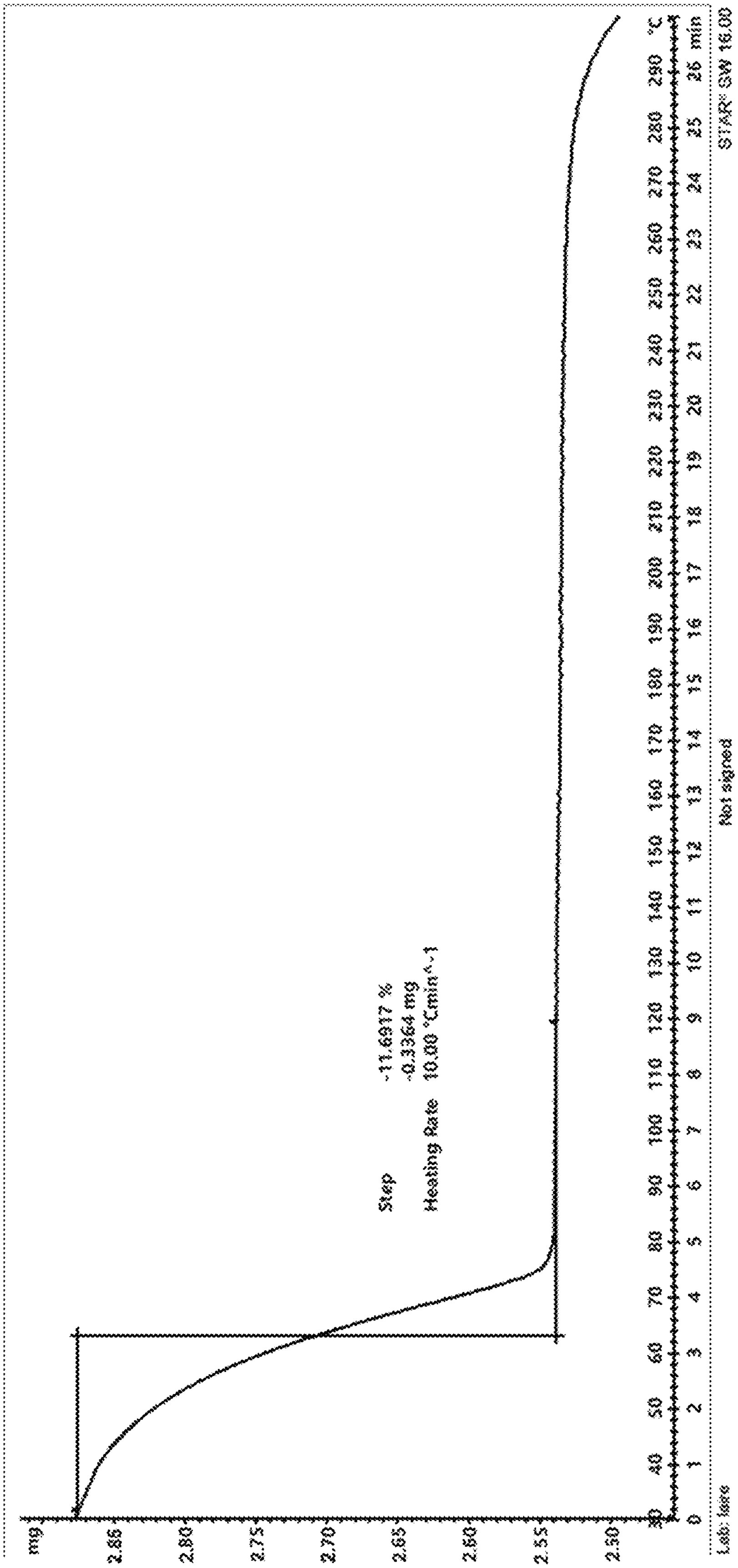
FIG. 3 shows a TGA profile of the crystal form α of fruquintinib.

The error of the TGA may be within about +0.5 mass %. Herein, "the TGA profile is substantially as shown in FIG. 3" means that the TGA profile is substantially the same as in FIG. 3, and the term "substantially the same" in the TGA profile means that such error changes are taken into account.

"Room temperature" described in the present application refers to a temperature of 10-25° C. Herein, unless otherwise stated, percentages are by weight.

Micro ED: Microcrystal Electron Diffraction

The crystal structure of the crystal form α described in the present application was determined and collected using the microcrystal electron diffraction (Micro ED) technique. The specific parameters are shown in the table below:

TABLE 2

| | | |
|---|---|---|
| Apparatus | Transmission electron microscope | Thermo Scientific Glacios |
| | Detector | Thermo Scientific Ceta-D |
| | Sample holder | Autoloader |
| Experimental condition | Voltage | 200 kV |
| | Temperature | 83 K |
| | Vacuum value | $10^{-7}$ Pa high vacuum |
| Software | Data collection | Thermo Scientific EPU-D |
| | Data processing | XDS, SHELXT, SHELXL |

Herein, the crystal form I, crystal form II, crystal form III, crystal form IV, crystal form VII, and crystal form VIII were crystal form I, crystal form II, crystal form III, crystal form IV, crystal form VII, and crystal form VIII prepared according to the method disclosed in CN106604919B. Herein, the crystal form C was crystal form C prepared according to the method disclosed in CN105777722 A.

Figure 2B:
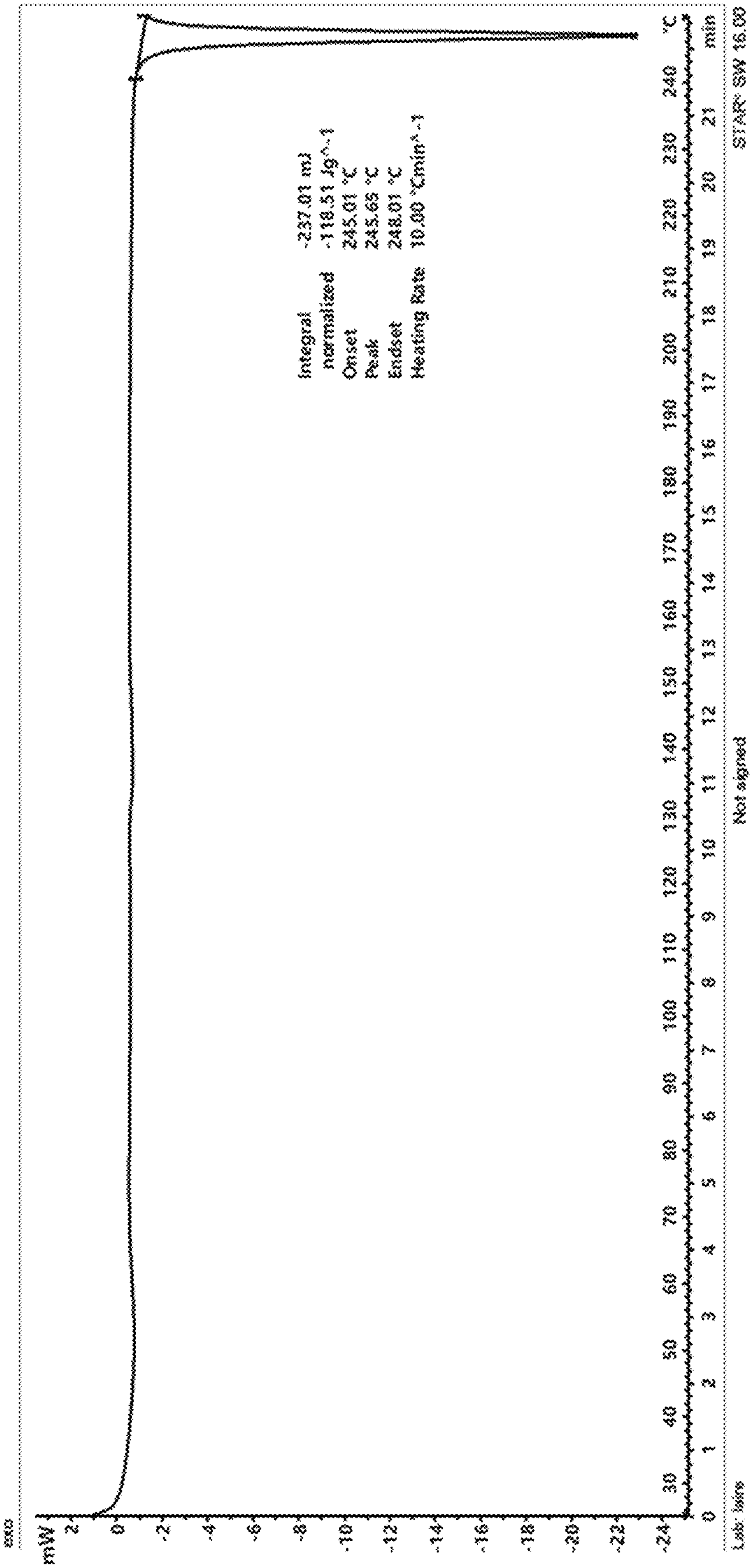
FIG. 2B shows a DSC profile of a crystal form C of fruquintinib.

The DSC profile of the crystal form C has an endothermic peak at about 245.65° C. The DSC profile of the crystal form C is substantially as shown in FIG. 2B.

Herein, fruquintinib, with the chemical name of 6-(6,7-dimethoxyquinazolin-4-yl-oxy)-N,2-dimethylbenzofuran-3-carboxamide, is a compound of formula (I):

formula (I)

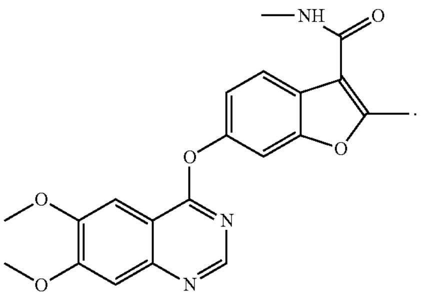

Example 1: Preparation of Crystal Form α of Fruquintinib 50 mg of fruquintinib and 5 mg of xylitol were weighed out and dissolved in 3.1 g of tetrahydrofuran at 50° C. The solution was sonicated at room temperature (10-25° C.) for 12 h and allowed to stand at 5° C. for 5 days to give the crystal form α of fruquintinib. The resulting solid (the crystal form α of fruquintinib) was collected and stored at a low temperature (5-10° C.) under nitrogen atmosphere.

The resulting crystal form α of fruquintinib was subjected to XRD analysis, DSC analysis, and TGA analysis. The XRD pattern of the crystal form α of fruquintinib is shown in FIG. 1A, the specific values of characteristic peaks are shown in Table 3, the DSC profile is shown in FIG. 2A, and the TGA profile is shown in FIG. 3.

TABLE 3

Characteristic peak data in XRD pattern of crystal form α of fruquintinib

| Position [°2θ] | Interplanar spacing [Å] | Area [cts*°2θ] | Relative intensity [%] |
|---|---|---|---|
| 4.8612 | 18.16356 | 196.52 | 2.36 |
| 7.2121 | 12.24728 | 4344.25 | 45.67 |
| 8.6433 | 10.22215 | 6432.51 | 67.63 |
| 9.7064 | 9.10482 | 35.32 | 0.37 |
| 12.0184 | 7.35801 | 1063.51 | 12.78 |
| 14.4445 | 6.12716 | 4105.90 | 49.33 |
| 15.1823 | 5.83104 | 9511.79 | 100.00 |
| 16.1711 | 5.47666 | 417.73 | 5.02 |
| 17.3163 | 5.11695 | 124.34 | 1.49 |
| 20.4232 | 4.34501 | 893.25 | 9.39 |
| 22.3484 | 3.97487 | 1535.76 | 14.35 |
| 23.9600 | 3.71103 | 833.72 | 8.77 |
| 24.4279 | 3.64099 | 69.22 | 1.16 |
| 25.3701 | 3.50787 | 45.60 | 0.64 |
| 26.0998 | 3.41143 | 682.97 | 8.21 |
| 26.4456 | 3.36760 | 456.78 | 5.49 |
| 28.3263 | 3.14814 | 49.94 | 0.60 |
| 28.6101 | 3.11756 | 65.45 | 1.10 |
| 29.1193 | 3.06418 | 1206.80 | 11.28 |
| 29.5981 | 3.01570 | 291.16 | 3.50 |
| 30.1883 | 2.95807 | 43.73 | 0.61 |
| 30.6296 | 2.91645 | 46.03 | 0.65 |
| 30.9004 | 2.89151 | 31.05 | 0.65 |
| 32.6561 | 2.73994 | 196.46 | 2.07 |
| 35.0678 | 2.55684 | 27.41 | 0.29 |
| 35.5106 | 2.52597 | 16.07 | 0.17 |
| 36.6421 | 2.45052 | 99.63 | 0.93 |
| 38.1485 | 2.35715 | 20.84 | 0.29 |
| 38.5746 | 2.33208 | 19.56 | 0.41 |
| 39.4277 | 2.28357 | 27.33 | 0.46 |

Example 2: Preparation of Crystal Form α of Fruquintinib 50 mg of fruquintinib and 2.5 mg of xylitol were weighed out and dissolved in 2.5 g of tetrahydrofuran at 50° C. The solution was sonicated at room temperature (10-25° C.) for 5 h and allowed to stand at 0° C. for 1 day. The resulting solid was collected and stored at a low temperature (5-10° C.) under nitrogen atmosphere to give the crystal form α of fruquintinib, and the XRD pattern was substantially consistent with FIG. 1A.

Example 3: Preparation of Crystal Form α of Fruquintinib 50 mg of fruquintinib and 10 mg of xylitol were weighed out and dissolved in 5.0 g of tetrahydrofuran at 50° C. The solution was sonicated at room temperature (10-25° C.) for 24 h and allowed to stand at 10° C. for 10 days. The resulting solid was collected and stored at a low temperature (5-10° C.) under nitrogen atmosphere to give the crystal form α of fruquintinib, and the XRD pattern was substantially consistent with FIG. 1A.

Example 4: Preparation of Crystal Form α of Fruquintinib 5.0 g of fruquintinib was weighed out and added to tetrahydrofuran (15.5 g) and water (5.0 g), and the mixture was heated to a reflux temperature for dissolution. 0.25 g of the crystal form α of fruquintinib prepared in Example 1 was added as a crystal seed, and the mixture was slowly cooled to 5° C. and stirred for suspension crystallization for 24 h. The resulting solid was collected to give 4.55 g of the crystal form α of fruquintinib. The Karl Fischer test results show that the water content was 11.90%, the yield was 86.67%, and the XRD pattern was substantially consistent with FIG. 1A.

Grinding step: 0.5 g of the crystal form α of fruquintinib prepared in Example 4 of the present application was weighed out and ground in a planetary ball mill at 60 HZ for about 30 s.

Figure 1B:
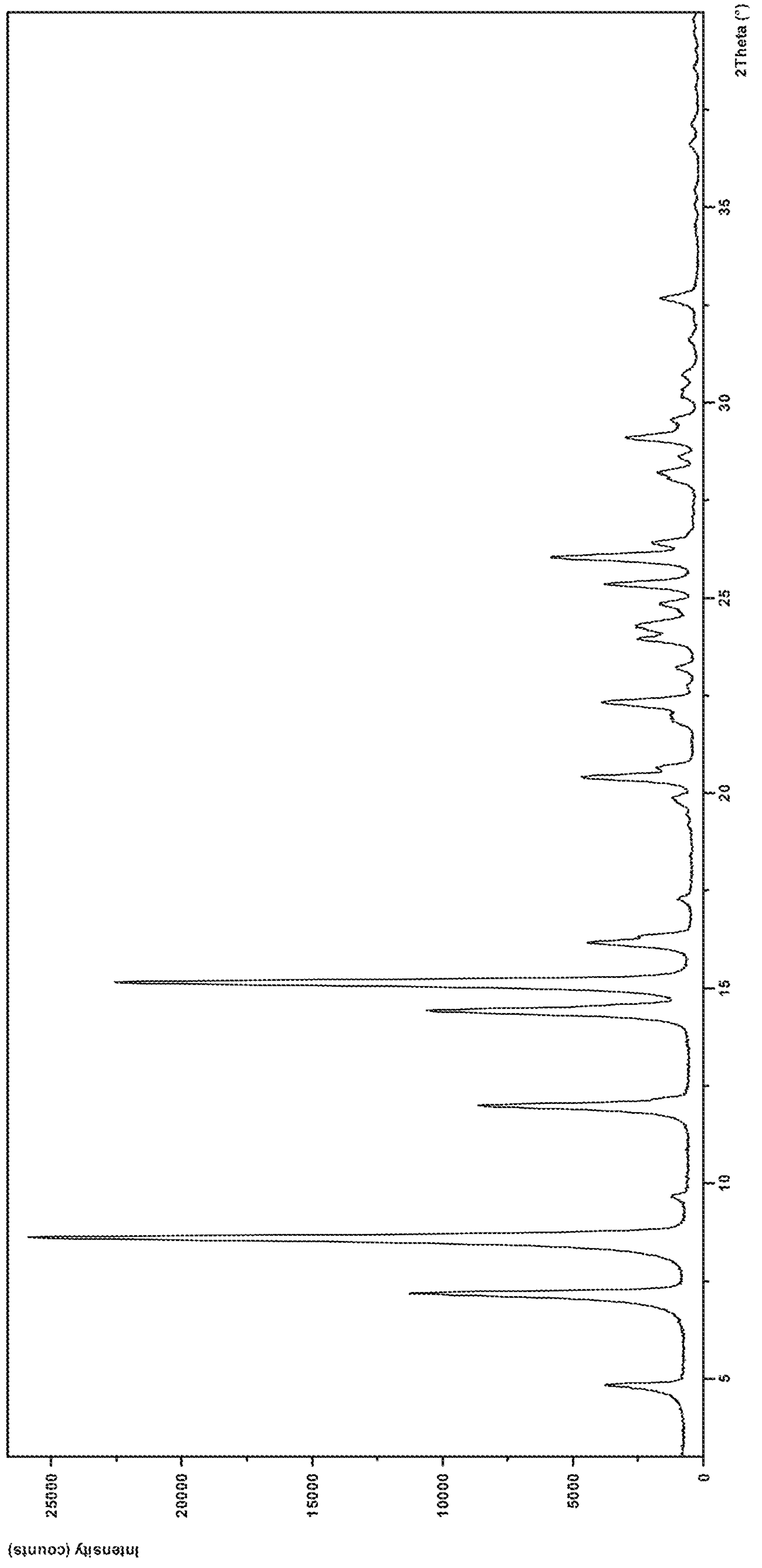
FIG. 1B shows an XRD pattern of the crystal form α of fruquintinib after grinding.

The XRD pattern after grinding was substantially consistent with FIG. 1B.

TABLE 3-2

Characteristic peak data in XRD pattern of crystal form α of fruquintinib after grinding

| Position [°2θ] | Interplanar spacing [Å] | Relative intensity [%] | Area [cts*°2θ] |
|---|---|---|---|
| 4.8453 | 18.22293 | 12.00 | 303.89 |
| 7.2027 | 12.26323 | 40.71 | 1288.80 |
| 8.6257 | 10.24298 | 100.00 | 3798.72 |
| 9.6844 | 9.12548 | 2.42 | 76.52 |
| 12.0038 | 7.36692 | 31.65 | 1001.85 |
| 14.4260 | 6.13499 | 39.69 | 1759.13 |
| 15.1679 | 5.83652 | 86.30 | 3278.14 |
| 16.1646 | 5.47883 | 15.70 | 497.15 |
| 17.3020 | 5.12114 | 1.80 | 56.83 |
| 19.8901 | 4.46024 | 2.86 | 72.52 |
| 20.4132 | 4.34710 | 16.91 | 642.52 |
| 20.6782 | 4.29198 | 5.05 | 127.97 |
| 21.8242 | 4.06913 | 2.87 | 108.89 |
| 22.3423 | 3.97594 | 13.48 | 597.50 |
| 22.7399 | 3.90731 | 0.89 | 22.66 |
| 23.2083 | 3.82950 | 2.52 | 95.73 |
| 23.9410 | 3.71393 | 8.27 | 261.64 |
| 24.2854 | 3.66204 | 8.82 | 502.35 |
| 24.8569 | 3.57912 | 5.17 | 196.39 |
| 25.3532 | 3.51017 | 13.50 | 512.72 |
| 26.0368 | 3.41954 | 21.93 | 971.93 |
| 26.4156 | 3.37135 | 6.54 | 207.17 |
| 28.0184 | 3.18204 | 3.77 | 95.39 |
| 28.2258 | 3.15912 | 5.48 | 208.26 |
| 28.6102 | 3.11754 | 2.59 | 81.94 |
| 29.0926 | 3.06694 | 10.58 | 469.00 |
| 29.5851 | 3.01699 | 3.49 | 132.47 |
| 30.1528 | 2.96148 | 2.19 | 69.18 |
| 30.7212 | 2.90796 | 2.20 | 97.38 |
| 31.6137 | 2.82787 | 1.19 | 45.30 |
| 32.6696 | 2.73884 | 5.53 | 210.04 |
| 35.0504 | 2.55807 | 0.51 | 26.01 |
| 35.4014 | 2.53351 | 0.49 | 21.63 |
| 36.5954 | 2.45354 | 1.34 | 42.27 |
| 37.1076 | 2.42084 | 0.97 | 36.95 |
| 38.0838 | 2.36100 | 0.33 | 12.62 |
| 38.6041 | 2.33037 | 0.60 | 19.04 |
| 39.4563 | 2.28198 | 0.60 | 22.87 |

Example 5: Preparation of Crystal Form α of Fruquintinib 5.0 g of fruquintinib was weighed out and added to tetrahydrofuran (7.5 g) and water (7.5 g), and the mixture was heated to a reflux temperature for dissolution. 0.05 g of the crystal form α of fruquintinib prepared in Example 4 was added as a crystal seed, and the mixture was slowly cooled to 0° C. and stirred for suspension crystallization for 12 h. The resulting solid was collected to give 4.05 g of the crystal form α of fruquintinib, with a yield of 80.20%. The XRD pattern was substantially consistent with FIG. 1A.

Example 6: Preparation of Crystal Form α of Fruquintinib 5.0 g of fruquintinib was weighed out and added to tetrahydrofuran (45.0 g) and water (5.0 g), and the mixture was heated to a reflux temperature for dissolution. 1.0 g of the crystal form α of fruquintinib prepared in Example 4 was added as a crystal seed, and the mixture was slowly cooled to 10° C. and stirred for suspension crystallization for 48 h. The resulting solid was collected to give 4.86 g of the crystal form α of fruquintinib, with a yield of 81.0%. The XRD pattern was substantially consistent with FIG. 1A.

Example 7: Preparation of Crystal Form α of Fruquintinib 1.0 g of fruquintinib was weighed out and added to tetrahydrofuran (26.7 g) and water (10.0 g), and the mixture was heated to a reflux temperature for dissolution. 0.05 g of the crystal form α of fruquintinib prepared in Example 1 was added as a crystal seed, and the mixture was slowly cooled to 5° C. and stirred for suspension crystallization for 24 h. The resulting solid was collected to give 0.85 g of the crystal form α of fruquintinib, with a yield of 85.00%. The XRD pattern was substantially consistent with FIG. 1A.

Figure 6:
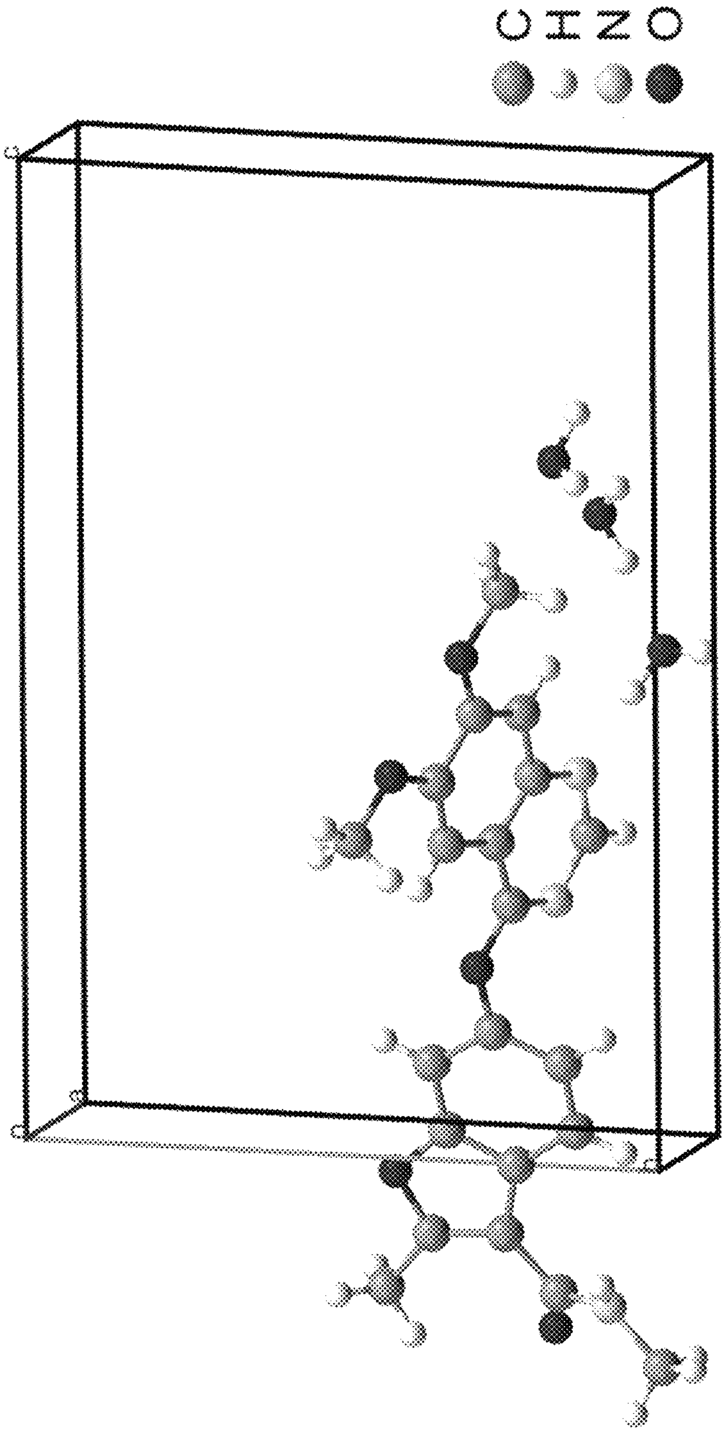
FIG. 6 shows an asymmetric unit diagram in a unit cell of the crystal form α of fruquintinib.

The crystal structure of the resulting crystal form α of fruquintinib was analyzed using the Micro ED technique. The asymmetric unit diagram in the unit cell of the crystal form α of fruquintinib is shown in FIG. 6, where Z' is 1, the asymmetric unit consists of 1 API molecule and $3H_2O$ molecules, and the crystal form α of fruquintinib is a trihydrate crystal form. The specific data of the crystal structure are shown in Table 4.

TABLE 4

Specific data of crystal structure of crystal form α of fruquintinib

| | |
|---|---|
| Chemical formula | $C_{21}H_{19}N_3O_5{\bullet}3H_2O$ |
| Molecular weight | 447.44 g · mol$^{-1}$ |
| Temperature | 83(2) K |
| Wavelength | 0.02508 Å |
| Crystal system, space group | Triclinic, P-1 (No. 2) |
| Unit cell parameters | a = 4.880(5) Å |
| | b = 11.98(2) Å |
| | c = 17.916(17) Å |
| | α = 89.10(6)° |
| | β = 94.56(10)° |
| | γ = 97.09(18)° |
| Volume | 1036(2) Å$^3$ |
| Z' | 1 |

Figure 1C:
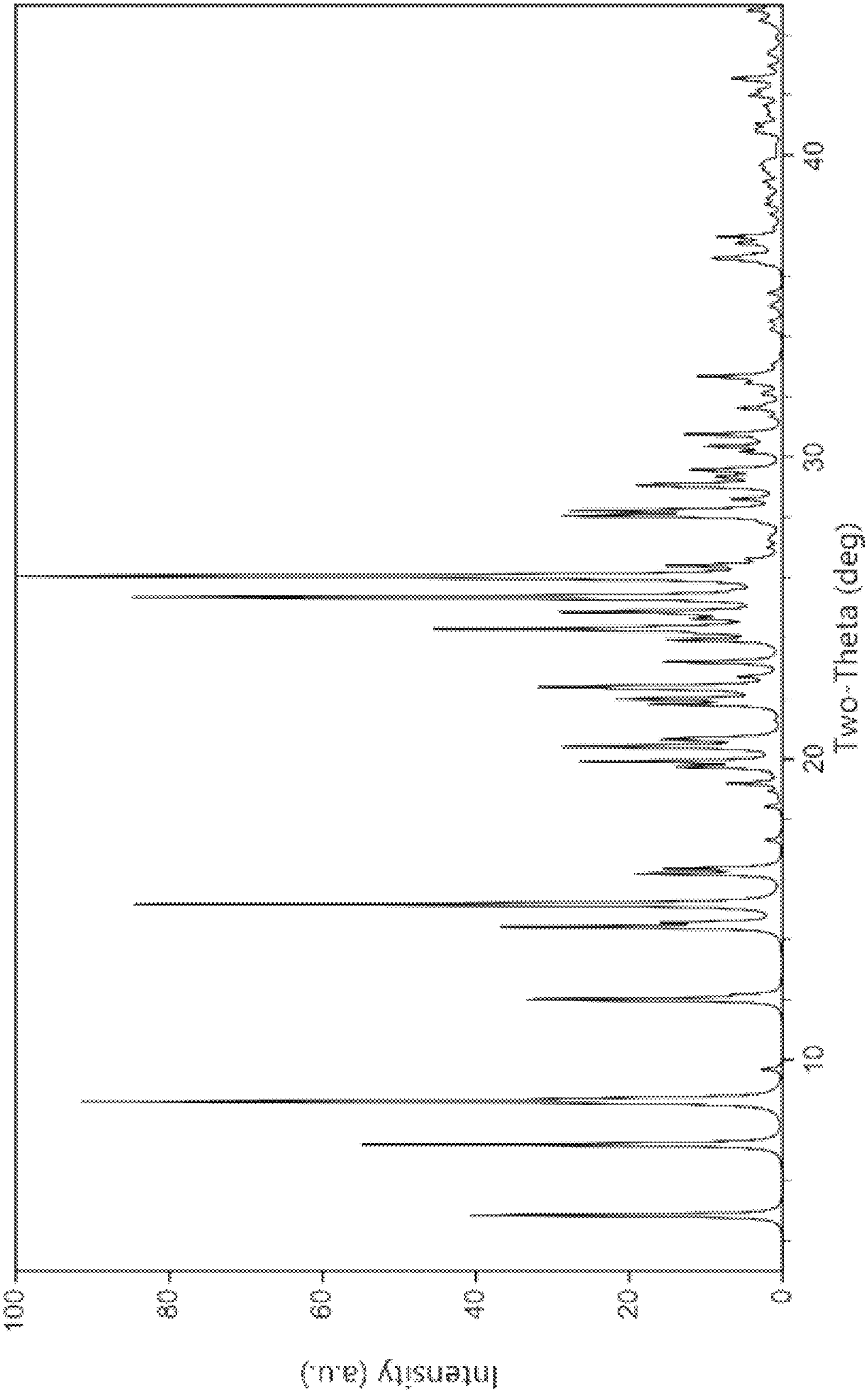
FIG. 1C shows a simulated XRD pattern of a single crystal of the crystal form α of fruquintinib.

FIG. 1C shows a simulated XRD pattern of a single crystal of the crystal form α of fruquintinib. Comparing FIG. 1B and FIG. 1C, it can be seen that the crystal form α of fruquintinib did not undergo polymorphic transition after grinding.

Example 8: Preparation of Crystal Form α of Fruquintinib 190.0 g of fruquintinib was weighed out and added to tetrahydrofuran (4058.4 g) and water (1140 g), and the mixture was heated to a reflux temperature for dissolution. 1.0 g of the crystal form α of fruquintinib prepared in Example 4 was added as a crystal seed, and the mixture was slowly cooled to 5° C. and stirred for suspension crystallization for 48 h. The resulting solid was collected to give 185.5 g of the crystal form α of fruquintinib, with a yield of 97.63%. The XRD pattern was substantially consistent with FIG. 1A.

Test Example 1: Stability Investigation of Crystal Forms of Fruquintinib

In order to investigate the storage stability of the crystal form α of fruquintinib prepared in Example 4 of the present application, the crystal form α (after grinding) of fruquintinib, the crystal form I and crystal form III disclosed in CN106604919B, and the crystal form C disclosed in CN105777722 A, samples were stored under stability conditions of 25° C./RH60% and 40° C./RH75% for 2 months and 6 months to investigate their crystal form stability. The results are shown in Table 5 below:

TABLE 5

| Stability tests for crystal form α, crystal form C, and crystal form III of fruquintinib | | | | | |
|---|---|---|---|---|---|
| Initial | | Investigation 1 | | Investigation 2 | |
| crystal form | Storage conditions | Storage time | Crystal form after storage | Storage time | Crystal form after storage |
| Crystal form α | 25° C./RH60% | 2 months | Crystal form α | 6 months | Crystal form α |
| | 40° C./RH75% | 2 months | Crystal form α | 6 months | Crystal form α |
| Crystal form α (after grinding) | 25° C./RH60% | 2 months | N/A | 6 months | Crystal form α |
| | 40° C./RH75% | 2 months | N/A | 6 months | Crystal form α |
| Crystal form III | 25° C./RH60% | 2 months | N/A | 6 months | Crystal form α + crystal form I |
| | 40° C./RH75% | 2 months | N/A | 6 months | Crystal form α + crystal form I |
| Crystal form C | 25° C./RH60% | 2 months | N/A | 6 months | Crystal form α + crystal form I |
| | 40° C./RH75% | 2 months | N/A | 6 months | Crystal form α + crystal form I |

Figure 4:
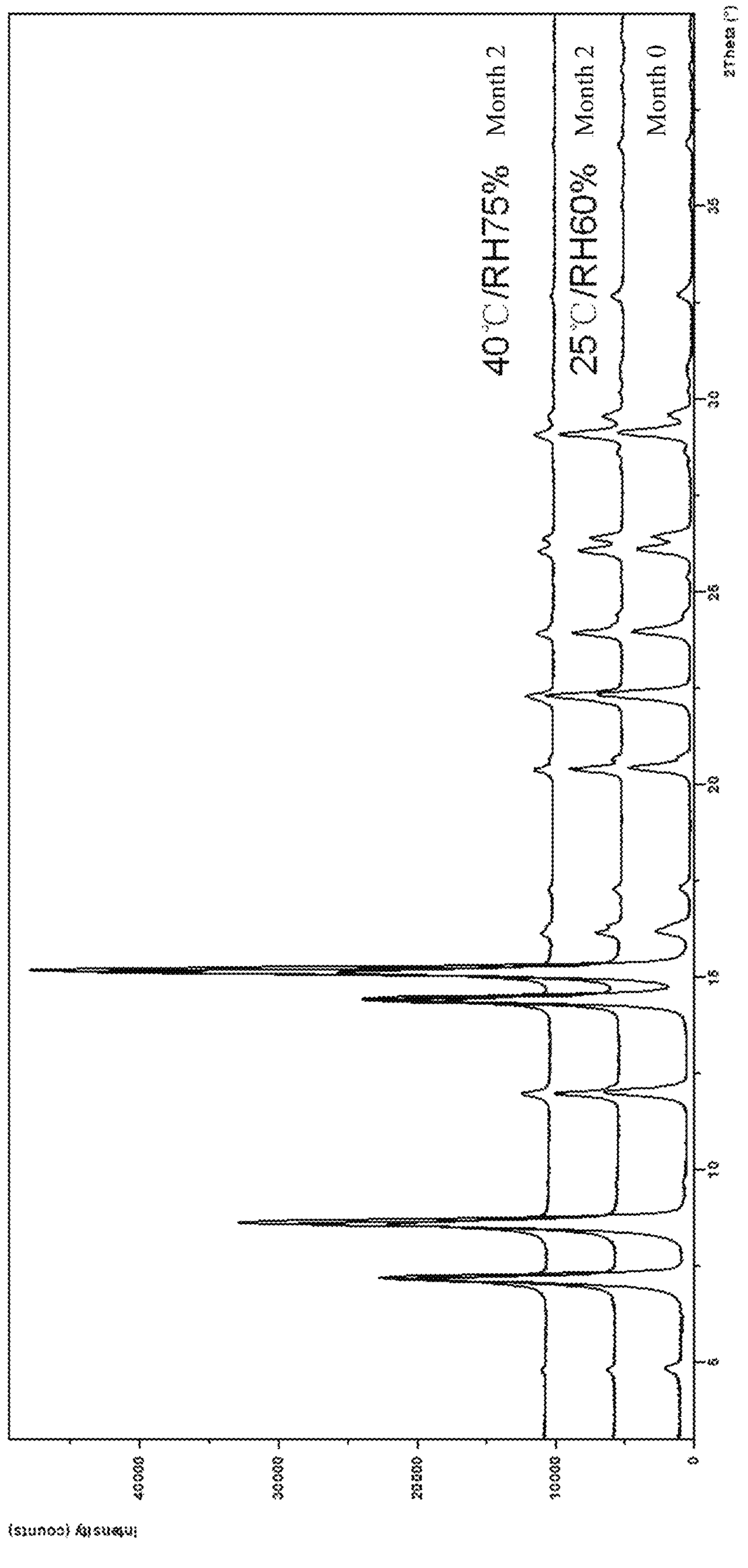
FIG. 4 shows a comparison of the crystal form α of fruquintinib after storage for 2 months for stability investigation.
Figure 5A:
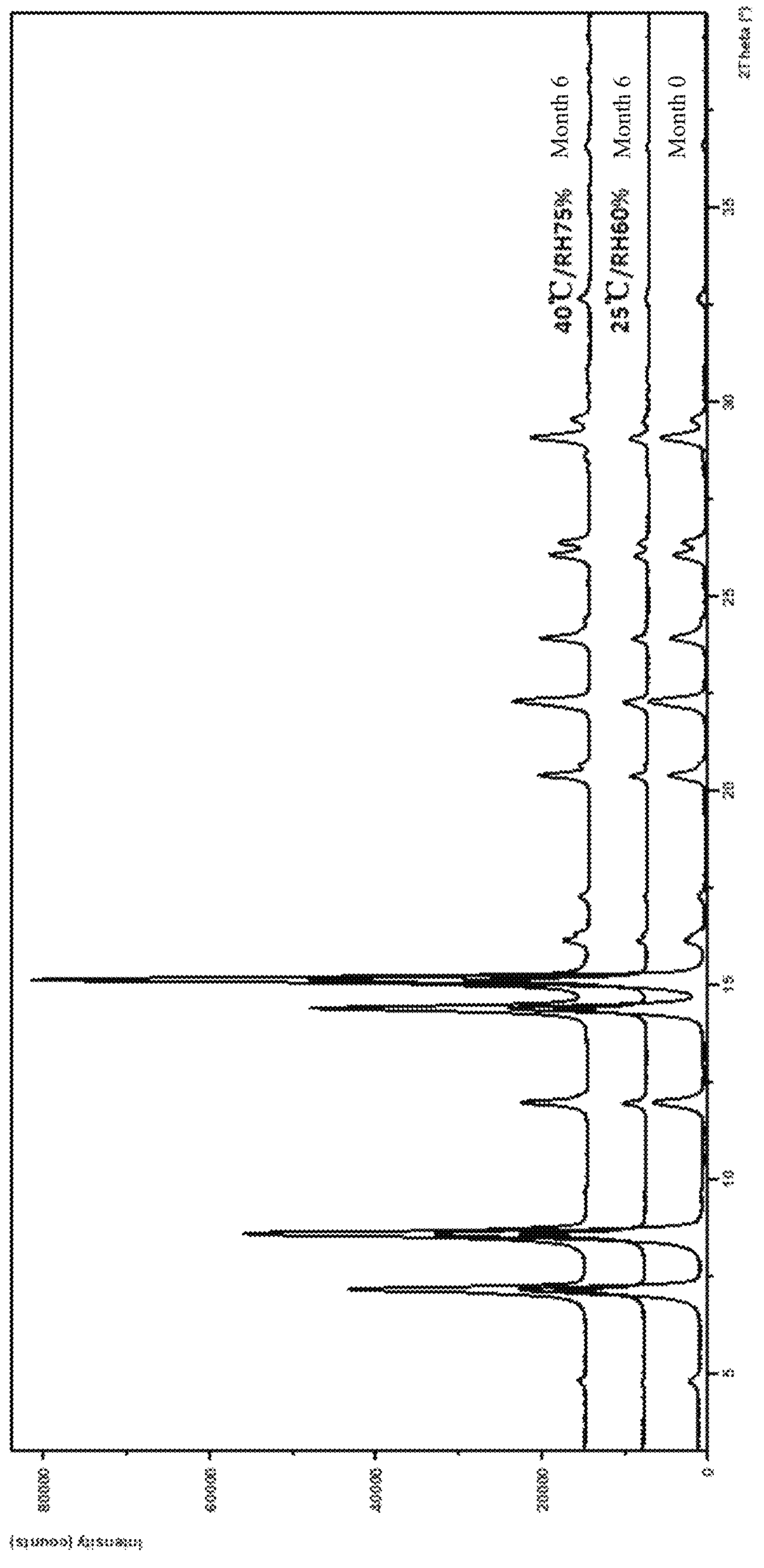
FIG. 5A shows a comparison of the crystal form α of fruquintinib after storage for 6 months for stability investigation.

Stability Test Results:

As shown in FIG. 4 (storage for 2 months) and FIG. 5A (storage for 6 months), the crystal form α of fruquintinib had good crystal form stability under the conditions investigated.

Figure 5B:
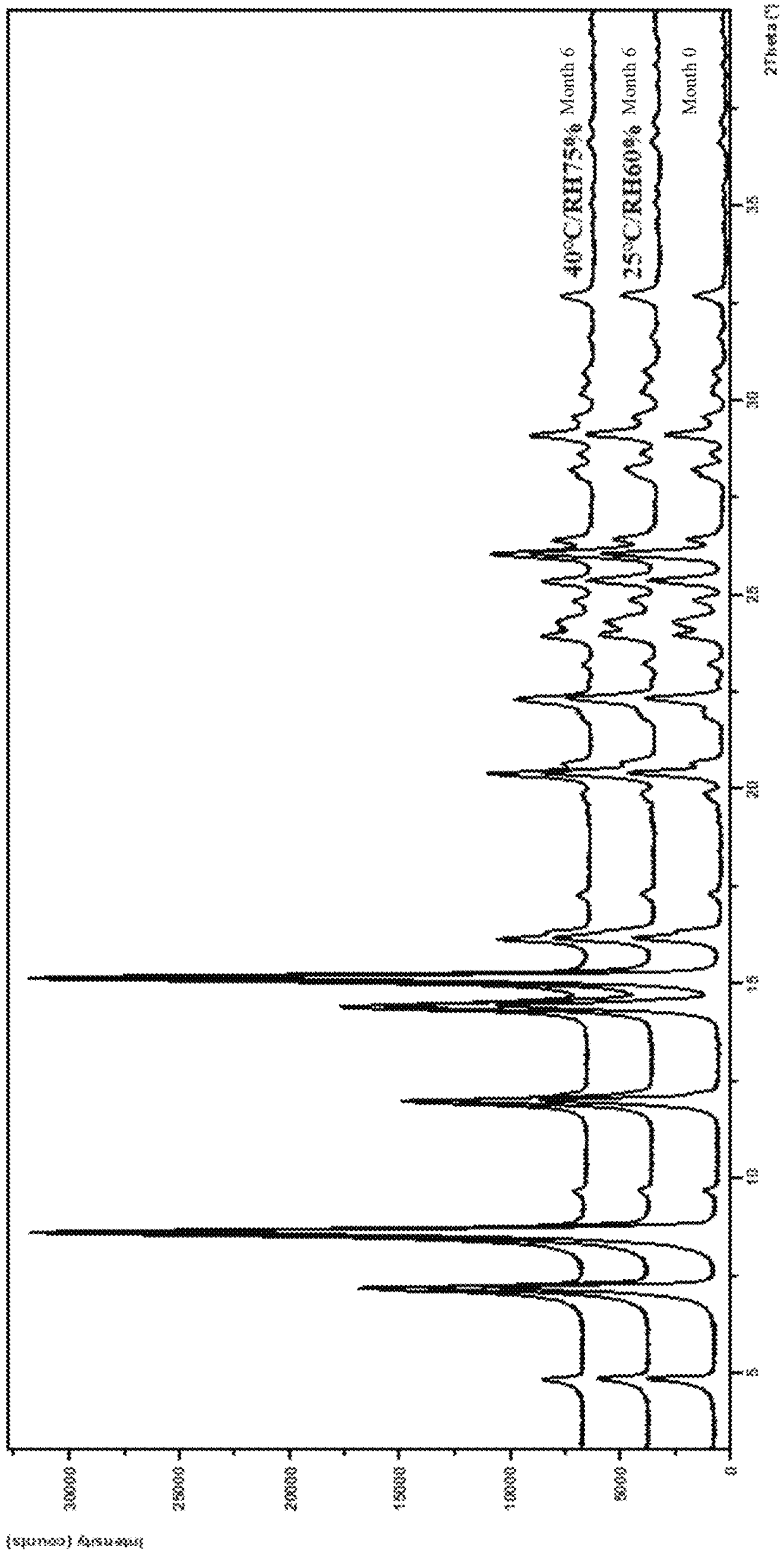
FIG. 5B shows a comparison of the crystal form α of fruquintinib after grinding and storage for 6 months for stability investigation.

As shown in FIG. 5B (storage for 6 months), the crystal form α of fruquintinib after grinding had good crystal form stability under the investigated conditions.

Test Example 2: Stability Investigation of Crystal Form α of Fruquintinib and Crystal Forms Disclosed in CN106604919B in Water The crystal form α of fruquintinib prepared in Example 4 of the present application, the crystal form I, crystal form II, crystal form III, crystal form VII, crystal form IV, and crystal form VIII disclosed in CN106604919B, and the crystal form C disclosed in CN105777722 A were suspended and stirred in water at different temperatures for 5 h and 24 h. The solids were filtered and subjected to XRD characterization. The results are shown in Table 6 below:

TABLE 6

| Stability tests for crystal form α of fruquintinib, crystal forms in CN106604919B, and crystal form C in water | | | | |
|---|---|---|---|---|
| Initial crystal form | Solvent | Temperature | Suspending and stirring for 5 h Crystal form | Suspending and stirring for 24 h Crystal form |
| Crystal form I | Water | 25° C. | Crystal form I | Crystal form α + crystal form I |
| Crystal form I | Water | 37° C. | Crystal form I | Crystal form α + crystal form I |
| Crystal form α | Water | 25° C. | Crystal form α | Crystal form α |
| Crystal form α | Water | 37° C. | Crystal form α | Crystal form α |
| Crystal form α + crystal form I (the mass ratio of the crystal form α to the crystal form I is 1:1) | Water | 25° C. | Crystal form α | Crystal form α |
| Crystal form α + crystal form I (the mass ratio of the crystal form α to the crystal form I is 1:1) | Water | 37° C. | Crystal form α | Crystal form α |
| Crystal form II | Water | 25° C. | Crystal form α | Crystal form α |
| Crystal form II | Water | 37° C. | Crystal form α | Crystal form α |
| Crystal form III | Water | 25° C. | Crystal form α | Crystal form α |
| Crystal form III | Water | 37° C. | Crystal form α | Crystal form α |
| Crystal form VII | Water | 25° C. | Crystal form α | Crystal form α |
| Crystal form VII | Water | 37° C. | Crystal form α | Crystal form α |
| Crystal form IV | Water | 25° C. | Crystal form α | Crystal form α |

TABLE 6-continued

| Stability tests for crystal form α of fruquintinib, crystal forms in CN106604919B, and crystal form C in water | | | | |
|---|---|---|---|---|
| Initial crystal form | Solvent | Temperature | Suspending and stirring for 5 h Crystal form | Suspending and stirring for 24 h Crystal form |
| Crystal form IV | Water | 37° C. | Crystal form α | Crystal form α |
| Crystal form VIII | Water | 25° C. | Crystal form α | Crystal form α |
| Crystal form VIII | Water | 37° C. | Crystal form α | Crystal form α |
| Crystal form C | Water | 25° C. | Crystal form α | Crystal form α |
| Crystal form C | Water | 37° C. | Crystal form α | Crystal form α |

The test results show that the crystal form α of fruquintinib had better crystal form stability than the crystal form I, crystal form II, crystal form III, crystal form VII, crystal form IV, crystal form VIII, and crystal form C in water.

The fruquintinib hydrate and the crystal form α thereof have good stability in water, provide a new option for the preparation of medicaments, and can be used for a wider medicament preparation process, such as wet granulation, thereby facilitating the improvement of the controllability and safety of drug quality.

Unless defined otherwise, technical and scientific terms used herein have the same meaning as commonly understood by those of ordinary skill in the art to which the present disclosure pertains. All patents, patent applications, and other publications are explicitly incorporated herein by reference for the purpose of description and disclosure. These publications are provided solely because they were disclosed prior to the filing date of the present application. All statements as to the dates of these documents or descriptions as to the contents of these documents are based on the information available to the applicant and do not constitute any admission as to the correctness of the dates or the content of these documents. Moreover, in any country or region, any reference to these publications herein shall not be construed as an admission that the publications form part of the commonly recognized knowledge in the art.

Those skilled in the art will recognize that the scope of the present application is not limited to the embodiments and examples described above. Instead, various modifications, replacements, or recombinations may be made without departing from the spirit of the present application, all of which fall within the protection scope of the present application.

The invention claimed is:

1. A fruquintinib hydrate of formula (II):

II

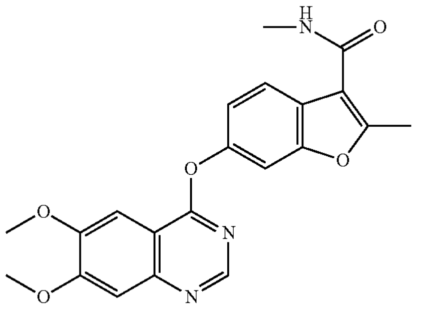

$\bullet n H_2O$, wherein n is 3, and the fruquintinib hydrate has an X-ray powder diffraction pattern with characteristic peaks at 2θ angles of 7.2±0.2°, 8.6±0.2°, 14.4±0.2°, 15.2±0.2°, 20.4±0.2°, 22.3±0.2°, 24.0±0.2°, 26.1±0.2°, 26.4±0.2°, and 29.1±0.2°.

2. The fruquintinib hydrate according to claim 1, wherein the X-ray powder diffraction pattern of the fruquintinib hydrate has characteristic peaks at 2θ angles of 4.9±0.2°, 7.2±0.2°, 8.6±0.2°, 12.0±0.2°, 14.4±0.2°, 15.2±0.2°, 16.2±0.2°, 20.4±0.2°, 22.3±0.2°, 24.0±0.2°, 25.4±0.2°, 26.1±0.2°, 26.4±0.2°, 28.3±0.2°, and 29.1±0.2°.

3. The fruquintinib hydrate according to claim 1, wherein the X-ray powder diffraction pattern of the fruquintinib hydrate has characteristic peaks at 2θ angles of 4.8±0.2°, 7.2±0.2°, 8.6±0.2°, 9.7±0.2°, 12.0±0.2°, 14.4±0.2°, 15.2±0.2°, 16.2±0.2°, 17.3±0.2°, 19.9±0.2°, 20.4±0.2°, 21.8±0.2°, 22.3±0.2°, 24.0±0.2°, 24.3±0.2°, 25.4±0.2°, 26.0±0.2°, 26.4±0.2°, 28.2±0.2°, 28.6±0.2°, 29.1±0.2°, 29.6±0.2°, and 32.7±0.2°.

4. The fruquintinib hydrate according to claim 1, wherein a Differential Scanning calorimetry (DSC) profile of the fruquintinib hydrate has endothermic peaks at 95.23±5° C. and 245.71±5° C.

5. The fruquintinib hydrate according to claim 1, wherein the fruquintinib hydrate is in a crystalline form of a triclinic crystal system, with a space group of P-1 (No. 2); a molecular weight of 447.44 $g \cdot mol^{-1}$; Z' of 1; the following unit cell parameters: a=4.880(5) Å, b=11.98(2) Å, c=17.916 (17) Å, a=89.10(6)°, β=94.56(10)°, and γ=97.09(18)°; and a unit cell volume of V=1036(2) $Å^3$.

6. A crystal form α of fruquintinib, wherein an X-ray powder diffraction pattern of the crystal form has characteristic peaks at 2θ angles of 7.2±0.2°, 8.6±0.2°, 14.4±0.2°, 15.2±0.2°, 20.4±0.2°, 22.3±0.2°, 24.0±0.2°, 26.1±0.2°, 26.4±0.2°, and 29.1±0.2°.

7. The crystal form α of fruquintinib according to claim 6, wherein a DSC profile of the crystal form α has endothermic peaks at 95.23±5° C. and 245.71±5° C.;

and/or, the crystal form α has a water content of 11.00±2.0%.

8. A preparation method for the fruquintinib hydrate according to claim 1, comprising: mixing fruquintinib and an additive in a solvent A and crystallizing, wherein the additive is a polyol and the solvent A is an ether solvent; or comprising (1) mixing fruquintinib in a solvent B, and heating for dissolution; and (2) adding a crystal seed of the hydrate and crystallizing, wherein the solvent B is a mixture of water and an ether solvent.

9. A preparation method for the crystal form α according to claim 6, comprising: mixing fruquintinib and an additive in a solvent A and crystallizing, wherein the additive is a polyol and the solvent A is an ether solvent; or comprising: (1) mixing fruquintinib in a solvent B, and heating for dissolution; and (2) adding a crystal seed of the crystal form α and crystallizing, wherein the solvent B is a mixture of water and an ether solvent.

10. The fruquintinib hydrate according to claim 1, wherein the X-ray powder diffraction pattern of the fruquintinib hydrate has characteristic peaks at 2θ angles of 4.9±0.2°, 7.2±0.2°, 8.6±0.2°, 12.0±0.2°, 14.4±0.2°, 15.2±0.2°, 16.2±0.2°, 17.3±0.2°, 20.4±0.2°, 22.3±0.2°, 24.0±0.2°, 24.4±0.2°, 25.4±0.2°, 26.1±0.2°, 26.4±0.2°, 28.3±0.2°, 28.6±0.2°, 29.1±0.2°, 29.6±0.2°, and 32.7±0.2°.

11. The fruquintinib hydrate according to claim 1, wherein the X-ray powder diffraction pattern of the fruquintinib hydrate has characteristic peaks at 2θ angles of 4.9±0.2°, 7.2±0.2°, 8.6±0.2°, 9.7±0.2°, 12.0±0.2°, 14.4±0.2°, 15.2±0.2°, 16.2±0.2°, 17.3±0.2°, 20.4±0.2°, 22.3±0.2°, 24.0±0.2°, 24.4±0.2°, 25.4±0.2°, 26.1±0.2°, 26.4±0.2°, 28.3±0.2°, 28.6±0.2°, 29.1±0.2°, 29.6±0.2°, and 32.7±0.2°.

12. The fruquintinib hydrate according to claim 1, wherein the X-ray powder diffraction pattern of the fruquintinib hydrate is substantially as shown in FIG. 1A, FIG. 1B, or FIG. 1C.

13. The fruquintinib hydrate according to claim 1, wherein, the DSC profile of the fruquintinib hydrate is substantially as shown in FIG. 2A; and/or, a Thermogravimetric Analysis (TGA) profile of the fruquintinib hydrate is substantially as shown in FIG. 3; and/or, the fruquintinib hydrate has a water content of 11.00±2.0%.

14. The fruquintinib hydrate according to claim 6, wherein the X-ray powder diffraction pattern of the fruquintinib crystal form α has characteristic peaks at 2θ angles of 4.9±0.2°, 7.2±0.2°, 8.6±0.2°, 12.0±0.2°, 14.4±0.2°, 15.2±0.2°, 16.2±0.2°, 20.4±0.2°, 22.3±0.2°, 24.0±0.2°, 25.4±0.2°, 26.1±0.2°, 26.4±0.2°, 28.3±0.2°, and 29.1±0.2°.

15. The fruquintinib hydrate according to claim 6, wherein the X-ray powder diffraction pattern of the fruquintinib hydrate crystal form α has characteristic peaks at 2θ angles of 4.8±0.2°, 7.2±0.2°, 8.6±0.2°, 9.7±0.2°, 12.0±0.2°, 14.4±0.2°, 15.2±0.2°, 16.2±0.2°, 17.3±0.2°, 19.9±0.2°, 20.4±0.2°, 21.8±0.2°, 22.3±0.2°, 24.0±0.2°, 24.3±0.2°, 25.4±0.2°, 26.0±0.2°, 26.4±0.2°, 28.2±0.2°, 28.6±0.2°, 29.1±0.2°, 29.6±0.2°, and 32.7±0.2°.

16. The fruquintinib hydrate according to claim 6, wherein, the X-ray powder diffraction pattern of the crystal form α is substantially as shown in FIG. 1A; and/or the DSC profile of the crystal form α is substantially as shown in FIG. 2A; and/or a TGA profile of the crystal form α is substantially as shown in FIG. 3.

17. A preparation method for the hydrate according to claim 8, comprising: mixing fruquintinib and an additive in a solvent A, ultrasonically dissolving the mixture, and allowing to stand for crystallization;

the additive is selected from one or more of xylitol, mannitol, sorbitol, isomaltitol, and maltitol;

the solvent A is selected from one or more of tetrahydrofuran, diethyl ether, propylene glycol methyl ether, methyl tert-butyl ether, isopropyl ether, and 1,4-dioxane;

and/or, fruquintinib and the additive are in a mass ratio of (5-20):1;

and/or, fruquintinib and the solvent A are in a mass-to-volume ratio of 1:(50-100);

and/or, the ultrasonic dissolution is performed at a temperature of 10-25° C.;

and/or, the ultrasonic dissolution is performed for an ultrasonic treatment period of 5-24 h;

and/or, the standing for crystallization is performed at a crystallization temperature of 0-10° C.;

and/or, the standing for crystallization is performed for a standing period of 1-10 days.

18. A preparation method for the hydrate according to claim 8, wherein, the ether solvent in the solvent B is one or more selected from tetrahydrofuran, diethyl ether, propylene glycol methyl ether, methyl tert-butyl ether, isopropyl ether, and 1,4-dioxane;

and/or, in solvent B, water and the ether solvent are in a mass ratio of 1:(1-9);

and/or, the crystal seed is used in an amount that is 1-20%, of a feeding amount of fruquintinib in step (1) by mass fraction;

and/or, step (2) comprises: adding the crystal seed, cooling to 0-10° C., and stirring for suspension crystallization for 12-48 h.

19. A preparation method for the hydrate according to claim 9, comprising: mixing fruquintinib and an additive in a solvent A, ultrasonically dissolving the mixture, and allowing to stand for crystallization;

the additive is one or more selected from xylitol, mannitol, sorbitol, isomaltitol, and maltitol; the solvent A is selected from one or more of tetrahydrofuran, diethyl ether, propylene glycol methyl ether, methyl tert-butyl ether, isopropyl ether, and 1,4-dioxane;

and/or, fruquintinib and the additive are in a mass ratio of (5-20):1;

and/or, fruquintinib and the solvent A are in a mass-to-volume ratio of 1:(50-100);

and/or, the ultrasonic dissolution is performed at a temperature of 10-25° C.;

and/or, the ultrasonic dissolution is performed for an ultrasonic treatment period of 5-24 h;

and/or, the standing for crystallization is performed at a crystallization temperature of 0-10° C.;

and/or, the standing for crystallization is performed for a standing period of 1-10 days.

20. A preparation method for the hydrate according to claim 9, wherein, the ether solvent in the solvent B is selected from one or more of tetrahydrofuran, diethyl ether, propylene glycol methyl ether, methyl tert-butyl ether, isopropyl ether, and 1,4-dioxane;

and/or, in solvent B, water and the ether solvent are in a mass ratio of 1:(1-9);

and/or, the crystal seed is used in an amount that is 1-20%, of a feeding amount of fruquintinib in step (1) by mass fraction;

and/or, step (2) comprises: adding the crystal seed, cooling to 0-10° C., and stirring for suspension crystallization for 12-48 h.

* * * * *